United States Patent [19]

Hayashi et al.

[11] Patent Number: 5,118,843

[45] Date of Patent: Jun. 2, 1992

[54] METHOD OF PRODUCING AN AGENT FOR TREATMENT OF CELLULOSE FABRIC

[75] Inventors: Yoshiyuki Hayashi, Otsu; Tadao Sasakura, Saitama, both of Japan

[73] Assignee: Nitto Boseki Co., Ltd., Fukushima, Japan

[21] Appl. No.: 596,054

[22] Filed: Oct. 11, 1990

[30] Foreign Application Priority Data

Oct. 14, 1989 [JP] Japan .................. 1-267795

[51] Int. Cl.$^5$ .................. C07F 9/02; C07F 9/22
[52] U.S. Cl. .................. 564/12
[58] Field of Search .................. 564/12; 428/276, 277

[56] References Cited

U.S. PATENT DOCUMENTS 2,661,311  6/1950  Jenkins .................. 428/276
3,712,789  1/1973  Linderman et al. .................. 428/276

FOREIGN PATENT DOCUMENTS 1176495  1/1970  United Kingdom .

Primary Examiner—Richard L. Raymond
Assistant Examiner—Shailendra Kumar
Attorney, Agent, or Firm—Darby & Darby

[57] ABSTRACT

Herein is disclosed a method of producing an agent for treatment of cellulose fabrics comprising phosphoryl amide compounds which comprises reacting phosphorus oxychloride with ammonia in a state that ammonia always exists either in a solvent comprising a lower alcohol or in a solvent mixture comprising 100 parts by weight of a lower alcohol and 15 parts by weight or less of water.

6 Claims, No Drawings

METHOD OF PRODUCING AN AGENT FOR TREATMENT OF CELLULOSE FABRIC

BACKGROUND OF THE INVENTION

This invention relates to a method of producing an agent for treatment of cellulose fabrics.

As an agent for treatment of cellulose fabrics, phosphoryl amide compounds have been used hitherto. The phosphoryl amide compounds are obtained by a reaction of phosphorus oxychloride and ammonia. For obtaining a phosphoryl amide compound by this reaction, the following methods have hitherto been adopted:

(1) a method for addition of phosphorus oxychloride into liquid ammonia;

(2) a method for addition of ammonia to a solution of phosphorus oxychloride in a halogenated hydrocarbon (U.S. Pat. No. 2,661,311);

(3) a method for addition of ammonia to a solution of phosphorus oxychloride in a hydrocarbon; and (4) a method for addition of phosphorus oxychloride to aqueous ammonia.

However, Method (1) mentioned above is disadvantageous in that the energy necessary for maintaining a low temperature is costly and the method requires to use a special apparatus. Method (2) is disadvantageous in that the insoluble intermediate is deposited in the system and necessitates a great power for its stirring and that, since the three chlorine groups of phosphorus oxychloride cannot completely be converted to amino group, the product contains unreacted chlorine groups and such a product is unsatisfactory for use as an agent for treatment of cellulose fabric.

Method (3) has the same fault as that of Method (2), and further it has problems that the hydrocarbon used as a solvent can partially be chlorinated and, since the hydrocarbon has a low flash point, there is a danger of ignition in the process of the reaction.

Method (4) has a problem that, since phosphorus oxychloride competitively reacts with water and ammonia, it is partially hydrolyzed to lower the yield of the intended product and a problem that a water-insoluble intermediate is formed. Further, the phosphoryl amide compound present in the resulting aqueous solution slowly undergoes hydrolysis in the process of concentration at elevated temperature or in the course of storage and transforms into a substance unsuitable as an agent for treatment of cellulose fabrics.

SUMMARY OF THE INVENTION

Accordingly, it is an object of this invention to provide a method of producing an agent for treatment of cellulose fabrics which overcomes the above disadvantages of the prior techniques, is safe and low in cost, has excellent quality and properties as an agent for treatment of cellulose fabric, and comprises a phosphoryl amide compound.

This invention provides a method of producing an agent for treatment of cellulose fabrics comprising phosphoryl amide compounds which comprises reacting phosphorus oxychloride with ammonia in a state that ammonia always exists in a solvent containing a lower alcohol.

This invention further provides a method of producing an agent for treatment of cellulose fabrics comprising phosphoryl amide compounds which comprises reacting phosphorus oxychloride with ammonia in a state that ammonia always exists in a solvent mixture comprising 100 parts by weight of a lower alcohol and 15 parts by weight or less of water.

DETAILED DESCRIPTION OF THE INVENTION

In this invention, as a solvent, a single solvent consisting of a lower alcohol only or a solvent mixture comprising 100 parts by weight of a lower alcohol and 15 parts by weight or less of water is used. If a quantity of water in the solvent mixture exceeds 15 parts by weight, a side reaction becomes readily taking place between phosphorus oxychloride and water, which brings about an undesirable result.

The lower alcohol preferably satisfies the following conditions:

(1) After use as a solvent, it can be recovered at a temperature of 100° C. or below under a reduced pressure.

(2) It dissolves the product. Examples of such a lower alcohol include unsubstituted and substituted lower alcohols such as methyl alcohol, ethyl alcohol, n-propyl alcohol, iso-propyl alcohol, n-butyl alcohol, iso-butyl alcohol, sec-butyl alcohol, tert-butyl alcohol, ethylene glycol, ethylene glycol monomethyl ether, hexafluoro-iso-propyl alcohol and the like.

If the solvents of this invention are used as a solvent, the following advantages are brought about:

(1) Since the product is readily soluble in the solvent, the reaction progresses homogeneously and the substitution readily takes place. Further, since a quantity of deposited product in the system is small, stirring can be effected sufficiently, owing to which the reaction heat can easily be removed, the production can be performed smoothly, and the power necessary for stirring can be small. Therefore, there is great significance in a scale of industrial manufacture.

(2) The solvent can easily be removed, the period of time required for production can be shortened, and no solvent remains in the product.

The reaction of this invention is carried out in a state that ammonia always exists in the solvent. As used herein, the terms "always exists" mean that more than stoichiometric quantity of ammonia, based on phosphorus oxychloride, always exists in the solvent before and during the reaction between phosphorus oxychloride and ammonia. If the reaction between phosphorus oxychloride and ammonia is carried out in a state that less than stoichiometric quantity of ammonia exists in the solvent, a side reaction takes place between phosphorus oxychloride and lower alcohol and/or water and a phosphoric triester and/or phosphoric acid are formed as by-products, as a result of which yield of the intended phosphoryl amide compound decreases. On the other hand, if the reaction is carried out in a state that ammonia always exists in the solvent, the above-mentioned side reactions decrease. In the state that ammonia always exists in the solvent, the concentration of the ammonia is preferably 0.1% by weight or more and particularly 0.5% by weight or more, based on the solvent. It is a surprising fact that the continued presence of such a small quantity of ammonia in the solvent is enough to suppress the side reactions between phosphorus oxychloride and lower alcohol and/or water which produce phosphoric triester and/or phosphoric acid.

In order to add phosphorus oxychloride and ammonia into a solvent in the state that ammonia always exists in the solvent and to make their reaction progress successfully, the quantities of phosphorus oxychloride and ammonia must be controlled so that no excessive phosphorus oxychloride exists in the reaction system. As a method for adding the phosphorus oxychloride and ammonia, dropwise addition may be adopted. Otherwise, a direct introduction of the reactants into the reaction system using an inlet tube may also be adopted.

Next, a particularly preferable procedure for the method of this invention for production of an agent for treatment of cellulose fabrics will be mentioned below.

The procedure consists of the following steps:

(1) adding anhydrous ammonia to a solvent of this invention, (2) adding phosphorus oxychloride and ammonia and reacting them, while maintaining a state that at least a predetermined quantity of ammonia always exists, and, (3) after the reaction, evaporating the reaction mixture to dryness under a reduced pressure to obtain a product which is an agent for treatment of cellulose fabrics comprising a phosphoryl amide compound.

The agent for treatment of cellulose fabrics obtained according to this invention is usually put to use in the form of an aqueous solution. Its particularly preferable use is a use as an agent for non-shrink treatment at the time of repeated washing of cellulose fabrics. When it is used as an agent for non-shrink treatment, its aqueous solution is attached to a cellulose fabrics. At this time, the aqueous solution may be used either singly or in combination with auxiliary components such as an acid catalyst (for example, diammonium hydrogen phosphate, ammonium chloride, organic amine hydrochloride, zinc chloride, magnesium chloride, zinc nitrate, zinc borofluoride, hydrochloric acid, phosphoric acid and the like), a small quantity of conventional resin treating agent, softener, penetrant, repellent, cellulose crosslinking agent and the like.

As a method for attaching an agent for treatment to fabrics, a method which comprises dipping fabrics into the aqueous solution and using dipped fabrics as they are or using the dipped fabrics after squeezing it with rolls or a mangle and a method which comprises spraying or coating the aqueous solution onto a fabric can be referred to.

As the quantity of the agent for treatment to be attached to the fabrics, 2 to 9% by weight as expressed in terms of the quantity of active ingredient based on the weight of the fabrics in dryness is preferable. If the quantity of the agent is smaller than the above, the non-shrink effect decreases. If its quantity exceeds the above, strength of the fabrics can decrease when the fabrics is made of some elementary materials.

The elementary base material (base fiber material) of the cellulose fabrics includes cellulosic fibers. For example, viscose rayon filament, viscose rayon staple, high-tenacity viscose rayon filament, high-tenacity viscose rayon staple, Polynosic, Cupra filament, Cupra staple, cotton, ramie, linen and the like can be referred to. Into the above-mentioned elementary base material, a small quantity of any other fibers than the elementary base material such as organic synthetic fibers (polyamide, polyester, polyacrylonitrile, polypropylene, Spandex and the like) and inorganic synthetic fibers (glass fiber, carbon fiber, silicon carbide fiber and the like) may be mixed. Further, the fabric may have any forms of woven fabric, knitted fabric, unwoven fabric, resin-treated fabric, sewn products, and the like.

After attaching the agent for treatment to fabrics, it is subjected to a heat treatment. The heat treatment may be practiced by using any heat sources such as hot air, infrared ray, microwave, steam, and the like. The heat treatment may be effected either once or repeatedly twice or more. Preferable temperature of the heat treatment is 100° C. to 170° C., and preferable period of the heat treatment is 1 minute to 10 minutes. The temperature and period may be appropriately selected so that the fabric is not injured. By the heat treatment, the agent for treatment is converted to a water-insoluble substance and fixed onto the fabric. Preferably, the fabric is then washed with hot water or the like in order to remove the water-soluble components present in the fabrics.

Preferably, the fabric after the treatment contains 0.6 to 1.5% by weight of phosphorus originated from the agent for treatment attached to the treated fabric based on the weight of the starting fabric.

DESCRIPTION OF PREFERRED EMBODIMENT

Next, this invention will be further illustrated by way of the following examples.

EXAMPLE 1

One hundred parts by weight of methyl alcohol was saturated with anhydrous ammonia, while cooling it at 10° C. and stirring it. Then, 30 parts by weight of phosphorus oxychloride was added thereto while adding anhydrous ammonia into the methyl alcohol to continuously ensure that the concentration of ammonia in the reaction system was always 0.1% by weight or above based on the methyl alcohol. Up to completion of the addition of phosphorus oxychloride, the reaction temperature was retained at 10° C. After completing the addition, the mixture was stirred at room temperature for 30 minutes to complete the reaction. At the end of the reaction, the quantity of the solid material deposited in the reaction system was about 20 parts by weight.

Next, the reaction mixture including the solid material was dried at 50° C. under a reduced pressure to distill off the volatile components such as methyl alcohol and the like to obtain 50 parts by weight of an agent for treatment of cellulose fabric. The period of time required for the drying under reduced pressure was 30 minutes.

The composition of the agent for treatment of cellulose fabric thus obtained was analyzed by 31P NMR and elementary analyses. As the result, the quantity of phosphoryl amide compound was 18.5% by weight and that of ammonium chloride was 31.5% by weight. Although the phosphoryl amide compound contained about 2% by weight of methyl ester group, it was water-soluble. In the product, no unsubstituted chlorine remained.

Then, the agent for treatment of cellulose fabric obtained above was dissolved into water to prepare a transparent aqueous solution having a concentration of 110 g/liter. A cotton knitted fabric (30 S/1, 26"×28GG, KANOKO, whiteness 127) dyed with a fluorescent brightner was immersed in said solution and squeezed with a pick-up of about 90%, and then dried at 100° C. and heat-treated at 150° C. for 2 minutes, after which the fabric was washed with hot water and dried. The treated fabric thus obtained had as excellent a whiteness as 118, and the yield of the agent for treatment fixed onto the treated fabric was as high as about 85%. When the treated fabric was repeatedly washed in a domestic washing machine ten times, its shrinkage percentage was 4% in the longitudinal direction and 6% in the lateral direction, demonstrating its excellent non-shrink performance.

COMPARATIVE EXAMPLE 1

With stirring, 30 parts by weight of phosphorus oxychloride was dissolved into 100 parts by weight of monochlorobenzene and cooled to 10° C. After adding anhydrous ammonia, the mixture was reacted with stirring at 10° C. for 30 minutes. After the reaction, the reaction mixture was dried under reduced pressure at 50° C. to distill off the volatile components such as monochlorobenzene and the like. Thus, 50 parts by weight of an agent for treatment of cellulose fabric was obtained. The period of time required for the drying under reduced pressure was 4 hours. The agent for treatment of cellulose fabric thus obtained contained about 2% by weight of monochlorobenzene. According to $^{31}P$ NMR analysis and elementary analysis, about 15% of chlorine group remained in it without substitution.

Next, the agent for treatment of cellulose fabric obtained in the above comparative example was dissolved into water to prepare an aqueous solution having a concentration of 110 g/liter. With the aqueous solution, a cellulose fabric was treated in the same manner as in Example 1. As a result, a light brown colored oily substance was noticeable on the surface and the whiteness was as bad as 110. Yield of the agent for treatment fixed onto the treated fabric was as low as about 75%. The shrinkage percentage was 7% in the longitudinal direction and 7% in the lateral direction, demonstrating an inferiority of the product of this example to that of Example 1.

EXAMPLE 2

One hundred parts by weight of ethyl alcohol was cooled to 7° C. and saturated with anhydrous ammonia with stirring. Then, 30 parts by weight of phosphorus oxychloride was added, while adding anhydrous ammonia to continuously ensure that the concentration of ammonia in the reaction system was always at least 0.1% by weight based on the ethyl alcohol. Up to completion of its addition, the reaction temperature was maintained at 7° C. After the addition, the reaction mixture was stirred at room temperature for 30 minutes to complete the reaction. At the end of the reaction, the quantity of solid material deposited in the reaction system was about 30 parts by weight. Next, the reaction mixture including the solid material was dried under reduced pressure to distill volatile components such as ethyl alcohol and the like. Thus, 50 parts by weight of an agent for treatment of cellulose fabric was obtained. The period of time required for the drying was 50 minutes. Composition of the agent for treatment of cellulose fabrics thus obtained was analyzed by $^{31}P$ NMR and elementary analyses. As the result, the quantity of phosphoryl amide compound was 18.5 parts by weight and that of ammonium chloride was 31.5 parts by weight. Although the phosphoryl amide compound contained about 1.5% by weight of ethyl ester group, it was watersoluble. In the product, no unsubstituted chlorine group remained.

Next, a cellulose fabric was treated with the agent for treatment of cellulose fabric obtained above in the same manner as in Example 1. As the result, a good result was obtained similarly to Example 1.

EXAMPLES 3-7

To 100 parts by weight of methyl alcohol was added 0 part by weight, 1 part by weight, 3 parts by weight, 6 parts by weight and 10 parts by weight of water, as separate experiments. While cooling each of the solvent thus prepared at 10° C. and stirring it, it was saturated with anhydrous ammonia. Then, 35 parts by weight of phosphorus oxychloride was added thereto, while adding anhydrous ammonia to continuously ensure that the concentration of ammonia in the reaction system was always at least 0.1% by weight based on the methyl alcohol. When the addition of phosphorus oxychloride and anhydrous ammonia were completed, the reaction temperature was 25° C. After completing the addition, the mixture was stirred at room temperature for 30 minutes to complete the reaction. Then, the reaction mixture including a solid material was dried under reduced pressure at 50° C. to distill off the volatile components such as methyl alcohol and the like. Thus, about 50 parts by weight of an agent for treatment of cellulose fabrics was obtained.

Next, the agent for treatment of cellulose fabric obtained above was dissolved into water to prepare a transparent aqueous solution having a concentration of 110 g/liter. A cotton knitted fabric (30 S/1, 30"×28GG, KANOKO whiteness 127) dyed with a fluorescent brightner was immersed in said solution and squeezed with a pick-up of about 90%, and then it was dried at 100° C. and heat-treated at 150° C. for 2 minutes, after which it was washed with hot water and dried. Whitenesses, phosphorus contents and shrinkage percentages upon washing of the treated fabrics thus obtained are summarized in Table 1.

It is apparent from the table that agents for treatment of cellulose fabric synthesized in solvents prepared by adding a small quantity of water to methyl alcohol were excellent in whiteness, phosphorus content and shrinkage percentage upon washing.

TABLE 1

| Example | Quantity of water added (parts by weight) | Whiteness | Phosphorus content in treated fabric (%) | Shrinkage percentage after washing 10 times in domestic washing machine (%) | |
|---|---|---|---|---|---|
| | | | | Longitudinal | Lateral |
| 3 | 0 | 118 | 0.65 | 5.3 | 6.7 |
| 4 | 1 | 121 | 0.80 | 5.0 | 6.0 |
| 5 | 3 | 122 | 0.85 | 4.3 | 5.7 |
| 6 | 6 | 123 | 0.83 | 5.0 | 5.7 |
| 7 | 10 | 125 | 0.70 | 5.7 | 6.0 |

According to this invention, there is provided a method of producing an agent for treatment of cellulose fabrics having the following points of advantage:

(1) It is prevented from occurrence of the side reaction between phosphorus oxychloride and a lower alcohol and/or water to produce phosphoric triester and/or phosphoric acid, and can give the intended phosphoryl amide compound in a high yield.

(2) Since the phosphoryl amide compound is relatively readily soluble into the lower alcohol, stirring can be effected sufficiently, owing to which the heat of reaction can easily be removed, the production progresses smoothly, the quantity of solid material deposited in the reaction system can be made small, and the power necessary for stirring can be small. These are advantageous from the viewpoint of industrial manufacture.

(3) The reaction progresses nearly completely, and unreacted chlorine group is hardly contained in the product.

(4) After completion of the reaction, the solvent can easily be removed, owing to which the period of time necessary for production can be shortened and no solvent remains in the product.

(5) The agent for treatment of cellulose fabric comprising a phosphoryl amide compound thus obtained is excellent in non-shrink performance.

What is claimed is:

1. A method of producing a phosphoryl amide which comprises reacting phosphorus oxychloride with ammonia in a solvent consisting of lower alcohol effective to dissolve phosphoryl amide formed in the reaction and under conditions such that ammonia is always present in the solvent mixture during said reaction.

2. A method according to claim 1, wherein said ammonia always exists in said solvent in an amount of 0.1 parts by weight or more per 100 parts by weight of the lower alcohol.

3. A method according to claim 2, wherein said lower alcohol is methyl alcohol or ethyl alcohol.

4. A method of producing a phosphoryl amide which comprises reacting phosphorus oxychloride with ammonia in a solvent mixture containing a lower alcohol and up to 15 parts by weight of water, based on 100 parts by weight of said lower alcohol, under conditions such that ammonia is always present in the solvent mixture during said reaction.

5. The method of claim 4 wherein the ammonia present in said solvent mixture is in an amount of at least 0.1 part of ammonia per 100 parts by weight of the solvent mixture.

6. A method according to claim 5, wherein said lower alcohol is methyl alcohol or ethyl alcohol.

* * * * *